(12) United States Patent
Wu et al.

(10) Patent No.: US 11,641,901 B2
(45) Date of Patent: May 9, 2023

(54) HIGH-TEMPERATURE VIRUS-KILLING MASK

(71) Applicant: Wuyi University, Jiangmen (CN)

(72) Inventors: Min Wu, Jiangmen (CN); Xinlin Li, Jiangmen (CN); Guowei Jiang, Jiangmen (CN); Gongfa Chen, Jiangmen (CN); Guangwei Chen, Jiangmen (CN)

(73) Assignee: WUYI UNIVERSITY, Jiangmen (CN)

( * ) Notice: Subject to any disclaimer, the term of this patent is extended or adjusted under 35 U.S.C. 154(b) by 554 days.

(21) Appl. No.: 16/840,887

(22) Filed: Apr. 6, 2020

(65) Prior Publication Data

US 2021/0259343 A1 Aug. 26, 2021

(30) Foreign Application Priority Data

Feb. 24, 2020 (CN) .......................... 202010112545.7

(51) Int. Cl.
| | | |
|---|---|---|
| *A42B 1/008* | (2021.01) | |
| *A42B 1/0182* | (2021.01) | |
| *A61M 16/10* | (2006.01) | |
| *A62B 18/02* | (2006.01) | |
| *A62B 18/10* | (2006.01) | |
| *A41D 13/11* | (2006.01) | |
| *A62B 23/02* | (2006.01) | |

(Continued)

(52) U.S. Cl.
CPC ............. *A42B 1/008* (2013.01); *A42B 1/0182* (2021.01); *A61M 16/1075* (2013.01); *A62B 18/025* (2013.01); *A62B 18/10* (2013.01); *A41D 13/11* (2013.01); *A61M 2205/3653* (2013.01); *A61M 2209/088* (2013.01); *A62B 23/02* (2013.01)

(58) Field of Classification Search
CPC ....... A42B 1/008; A42B 1/0182; A42B 1/017; A42B 1/18; A42B 3/28; A61M 16/1075; A61M 2209/088; A61M 2205/3653; A61M 16/021; A61M 2205/3368; A61M 2205/36; A62B 18/025; A62B 18/10; A62B 23/02; A62B 9/003; A41D 13/11; A41D 2400/12; A61L 9/16; A42C 5/04
See application file for complete search history.

(56) References Cited

U.S. PATENT DOCUMENTS

| | | | | |
|---|---|---|---|---|
| 2006/0260183 A1* | 11/2006 | Hockaday | ............... | A01M 1/02 43/132.1 |
| 2011/0041237 A1* | 2/2011 | Gupta | ............... | A61M 16/0666 128/203.12 |

(Continued)

FOREIGN PATENT DOCUMENTS

| | | | | |
|---|---|---|---|---|
| CN | 203556072 U | * | 4/2014 | ............. A41D 13/11 |
| CN | 205360286 U | * | 7/2016 | |

(Continued)

*Primary Examiner* — Kendra D Carter
*Assistant Examiner* — Mautin I Ashimiu
(74) *Attorney, Agent, or Firm* — Vivacqua Crane, PLLC

(57) ABSTRACT

Disclosed is a high-temperature virus-killing mask, including a sunhat, a heating component and a mask body. The heating component comprises a high-temperature microtube and a base, both arranged in the sunhat. The high-temperature microtube is provide with a resistance wire which may be energized to generate heat to enable the temperature in the high-temperature microtube to rise up to about 200° C.

10 Claims, 6 Drawing Sheets

(51) Int. Cl.
  *A62B 9/00*      (2006.01)
  *A42B 1/017*     (2021.01)
  *A42B 1/18*      (2006.01)
  *A61L 9/16*      (2006.01)

(56) References Cited

U.S. PATENT DOCUMENTS

2013/0284169 A1\* 10/2013 Foote .................... A61M 16/16
                                                  128/203.14
2014/0053318 A1\*  2/2014 Fitzgerald .......... H04N 5/23229
                                                    2/209.13
2017/0361133 A1\* 12/2017 Yu ......................... F04D 25/084
2018/0064199 A1\*  3/2018 Battis ................... F28D 9/0093

FOREIGN PATENT DOCUMENTS

| CN | 108634443 A | \* | 10/2018 | ............. A41D 13/11 |
| CN | 109349704 A | \* | 2/2019 | ............. A42B 1/008 |
| JP | 5706008 B2 | \* | 4/2015 | ............. A42B 1/008 |

\* cited by examiner

HIGH-TEMPERATURE VIRUS-KILLING MASK

CROSS-REFERENCE TO RELATED APPLICATIONS

This application is based on and claims the benefit of priority from Chinese Patent Application No. 2020101125457, filed on 24 Feb. 2020, the entirety of which is incorporated by reference herein.

TECHNICAL FIELD

The disclosure relates to the technical field of health protection articles, and in particular to a high-temperature virus-killing mask.

BACKGROUND

Outbreaks of 2019 Novel Coronavirus Pneumonia (NCP), also referred to as COVID-19, have gain world's attention recently. Persons infected with this virus have symptoms of varying degrees. The infected persons will have a fever or slight cough, or will catch pneumonia, or even die. The NCP is mainly spread through respiratory droplets, so wearing a mask has become an important prevention approach. For most of existing masks, the outside air is directly filtered by a filter layer or a breather valve on the mask and then inhaled. The protective effect of such masks will be continuously weakened over time, so it is necessary to replace the mask for many times. However, under the current epidemic situation, the masks are far in short supply.

SUMMARY

The disclosure is aimed at solving at least one of the above technical problems in the related art to a certain extent. Hence, the disclosure provides a high-temperature virus-killing mask, in which a resistance wire can generate heat to allow the temperature in a high-temperature microtube to reach 200° C., so that NCP in air flowing through the high-temperature microtube is killed by the high temperature, and the physical health of a wearer can be effectively protected. In addition, the high-temperature virus-killing mask can be reused for many times, so that the problem of large usage of conventional disposable masks is solved.

In accordance with the embodiments of the disclosure, a high-temperature virus-killing mask is provided, including: a sunhat, a heating component, and a mask body. The heating component includes a high-temperature microtube and a base both arranged in the sunhat. A positive electrode is arranged at an upper end of the high-temperature microtube close to a middle portion thereof, and a negative electrode is arranged at a lower end of the high-temperature microtube close to the middle portion thereof. A resistance wire is arranged in the high-temperature microtube, two ends of the resistance wire are electrically connected to the positive electrode and the negative electrode, respectively. A positive terminal and a negative terminal are arranged on the base, respectively, and the positive electrode and the negative electrode are clamped in the positive terminal and the negative terminal, respectively. The base is electrically connected to a charge port through an electric wire, and when in use, the charge port is electrically connected to a power source. An upper end portion of the high-temperature microtube extends outside the sunhat to facilitate air inhalation, and a lower end portion of the high-temperature microtube is communicated with a cooling tube. A breather valve is arranged on an outer surface of the mask body, the breather valve is communicated with a rubber hose, and an air inlet end of the rubber hose is connected to an air outlet end of the cooling tube.

The high-temperature virus-killing mask according to the embodiments of the disclosure has at least the following technical effects. The high-temperature microtube is arranged in the sunhat, and power is supplied by the power source when in use, so that the resistance wire is energized to generate heat and the temperature in the high-temperature microtube rises up to about 200° C. Subsequently, when a user inhales air, the outside air is inhaled into the high-temperature microtube. Since NCP will be killed at a temperature of above 56° C., NCP in air flowing through the high-temperature microtube is killed by the high temperature. Then, the high-temperature disinfected air is cooled to the normal temperature by the cooling tube, and then filtered by the breather valve on the mask body and inhaled by the wearer. Thus, the air inhaled into the wear's nose does not contain NCP, so that the physical heath of the wearer can be effectively protected. In addition, the high-temperature virus-killing mask can be reused for many times, so that the problem of large usage of conventional disposable masks is solved. Moreover, since the positive electrode and the negative electrode of the high-temperature microtube are clamped in the positive terminal and the negative terminal of the base, respectively, the high-temperature microtube can be detached from the base for replacement and maintenance when the high-temperature microtube or the resistance wire is damaged, so that it is easy to operate.

In accordance with some embodiments of the disclosure, a first switch button for controlling the on/off of the circuit is connected in series on the electric wire, and the first switch button is arranged on an outer surface of the sunhat.

In accordance with some embodiments of the disclosure, the power source is a power bank which is electrically connected to the charge port through a USB data line, and a second switch button is arranged on the USB data line.

In accordance with some embodiments of the disclosure, the cooling tube is an elbow tube which is wound around a body of the sunhat for 2 to 4 times.

In accordance with some embodiments of the disclosure, the sunhat is a peaked cap, the cooling tube is wound around a body of the peaked cap for 4 times, and an air outlet end of the cooling tube extends out from a peaked portion of the peaked cap to be communicated with an air inlet port of the rubber hose.

In accordance with some embodiments of the disclosure, an air inlet/outlet tube is arranged in a middle portion of the breather valve, an outer thread is arranged at an end of the air inlet/outlet tube away from the breather valve, and an inner thread matched with the outer thread is arranged in an air outlet end of the rubber hose.

In accordance with some embodiments of the disclosure, the high-temperature microtube is a ceramic tube, and a heat preservation layer is arranged on an outer surface of the ceramic tube.

In accordance with some embodiments of the disclosure, the cooling tube is a copper tube, and a thermal insulating layer is arranged on an outer surface of the copper tube.

In accordance with some embodiments of the disclosure, the mask body is a KN95 protective mask with a breather valve.

In accordance with some embodiments of the disclosure, the high-temperature microtube has a length of 20 mm, an outer diameter of 4 mm and a wall thickness of 0.5 mm.

Additional aspects and advantages of the disclosure will be partially appreciated and become apparent from the description below, or will be well learned from the practices of the disclosure.

BRIEF DESCRIPTION OF THE DRAWINGS

The Above and/or Additional Aspects and Advantages of the Disclosure Will Become Apparent and Readily Comprehensible from the Following Description of Embodiments with Reference to the Accompanying Drawings, in which.

Figure 1:
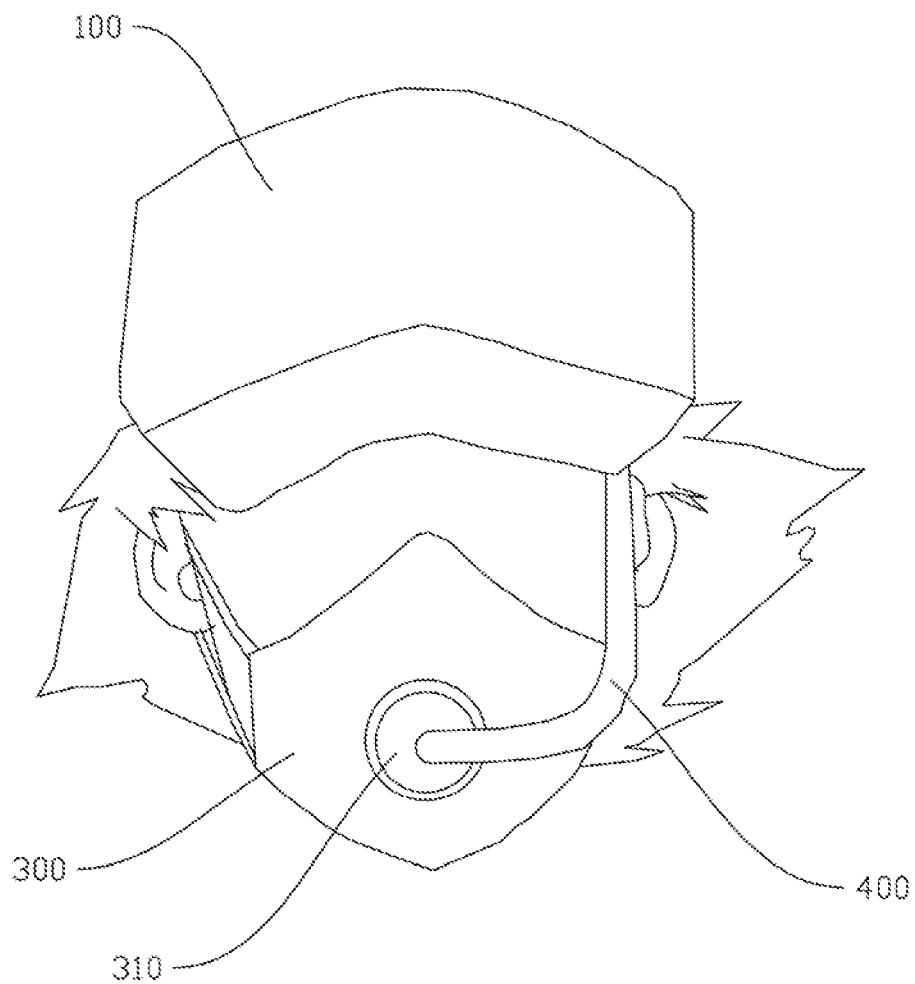
FIG. 1 is a schematic view of a usage state according to an embodiment of the disclosure.
Figure 2:
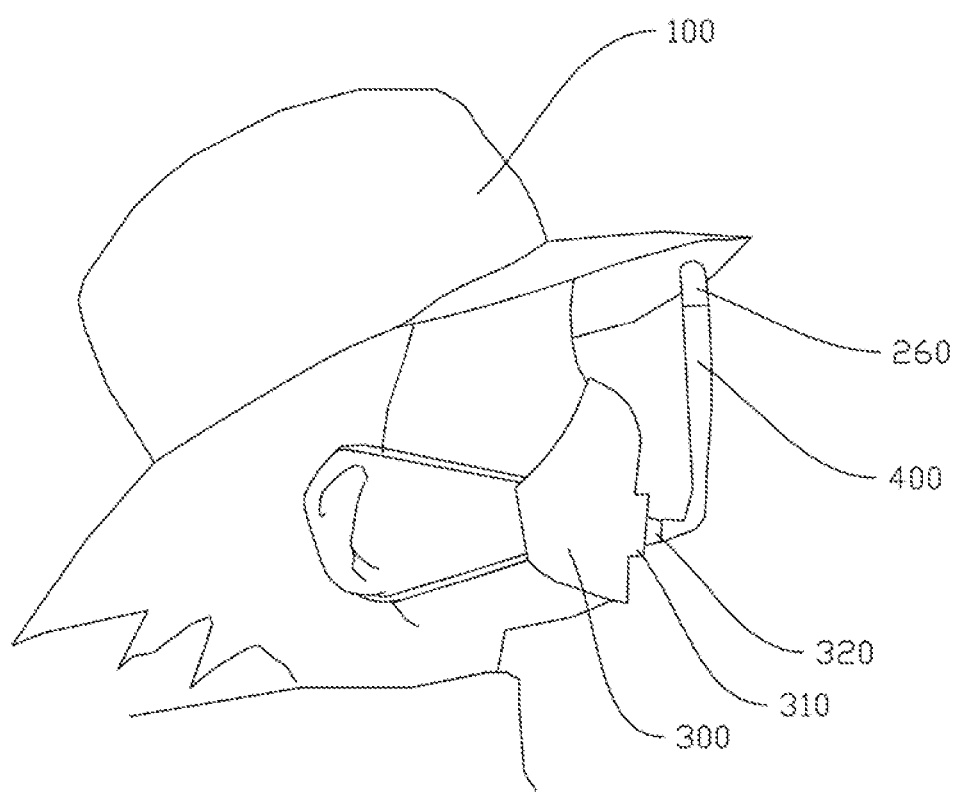
FIG. 2 is a side view of FIG. 1.

LIST OF REFERENCE NUMERALS 100 sunhat
210 high-temperature microtube
220 base
230 resistance wire
240 electric wire
250 charge port
260 cooling tube
270 first switch button
271 second switch button
280 USB data line
290 power source
300 mask body
310 breather valve
320 air inlet/outlet tube
321 outer thread
330 filter
400 rubber hose
410 inner thread

DETAILED DESCRIPTION

Specific embodiments of the disclosure will be described in detail in this section, and the preferred embodiments of the disclosure are shown in the accompanying drawings. The accompanying drawings are used for supplementing the written description graphically so that each technical feature and the overall technical solution of the disclosure can be understood intuitively and visually. However, it should not be regarded as limiting the protection scope of the disclosure.

In the description of the disclosure, it should be understood that, the orientation or position relation indicated by the terms "upper", "lower", "front", "rear", "left", "right" or the like is an orientation or position relation shown in the accompanying drawings, merely for describing the disclosure and simplifying the description rather than indicating or implying that the specified device or element must have a particular orientation or be constructed and operated in a particular orientation. Therefore, it should not be interpreted as limitations to the disclosure.

In the description of the disclosure, the terms "first" and "second" are merely used for distinguishing the technical features, rather than implying or indicating relative importance or implicitly indicating the number of the involved technical features or the precedence relationship between the involved technical features.

In the description of the disclosure, unless otherwise explicitly defined, the terms "arrange", "mount", "connect" or the like shall be interpreted in a broad sense. The specific meanings of these terms in the disclosure can be reasonably determined in combination with the specific contents of the technical solutions by those skilled in the art.

With reference to FIGS. 1-6, a high-temperature virus-killing mask is provided according to an embodiment of the disclosure, including: a sunhat 100, a heating component and a mask body 300. The heating component includes a high-temperature microtube 210 and a base 220 both arranged in the sunhat 100. A positive electrode is arranged at an upper end of the high-temperature microtube 210 close to a middle portion thereof, and a negative electrode is arranged at a lower end of the high-temperature microtube 210 close to the middle portion thereof. A resistance wire 230 is arranged in the high-temperature microtube 210. Two ends of the resistance wire 230 are electrically connected to the positive electrode and the negative electrode, respectively. A positive terminal and a negative terminal are arranged on the base 220, respectively. The positive electrode and the negative electrode are clamped in the positive terminal and the negative terminal, respectively. The base 220 is electrically connected to a charge port 250 through an electric wire 240. When in use, the charge port 250 is electrically connected to a power source 290. An upper end portion of the high-temperature microtube 210 extends outside the sunhat 100 to facilitate air inhalation, and a lower end portion of the high-temperature microtube 210 is communicated with a cooling tube 260. A breather valve 310 is arranged on an outer surface of the mask body 300. The breather valve 310 is communicated with a rubber hose 400. An air inlet end of the rubber hose 400 is connected to an air outlet end of the cooling tube 260. In the embodiment of the disclosure, the high-temperature microtube 210 is arranged in the sunhat 100, and power is supplied by the power source 290 when in use, so that the resistance wire 230 is energized to generate heat and the temperature in the high-temperature microtube 210 rises up to about 200° C. Subsequently, when a user inhales, the outside air is inhaled into the high-temperature microtube 210. Since NCP will be killed at a temperature of above 56° C., NCP in air flowing through the high-temperature microtube 210 is killed by the high temperature. Then, the high-temperature disinfected air is cooled to the normal temperature by the cooling tube 260, and then filtered by a filter 330 of the breather valve 310 on the mask body 300 and inhaled by the wearer. Thus, the air inhaled into the wear's nose does not contain NCP, so that the physical heath of the wearer can be effectively protected. In addition, the high-temperature virus-killing mask can be reused for many times, so that the problem of large usage of conventional disposable masks is solved. Moreover, since the positive electrode and the negative electrode of the high-temperature microtube 210 are clamped in the positive terminal and the negative terminal of the base 220, respectively, the high-temperature microtube 210 can be detached from the base 220 for replacement and maintenance when the high-temperature microtube 210 or the resistance wire 230 is damaged, so that it is easy to operate. The disclosure provides a facility for improvement of the commercially-available masks with a breather valve 310, and structures such as the sunhat 100 and the heating component can be additionally provided on the existing commercially-available masks with a breather valve 310, so that masks with better protective effects are obtained by improving the commercially-available masks with a breather valve 310. Moreover, the service life of the masks can be prolonged, the consumption of the existing commercially-available masks with a breather valve 310 can be reduced, and the current supply pressure of masks can be reduced.

Figure 3:
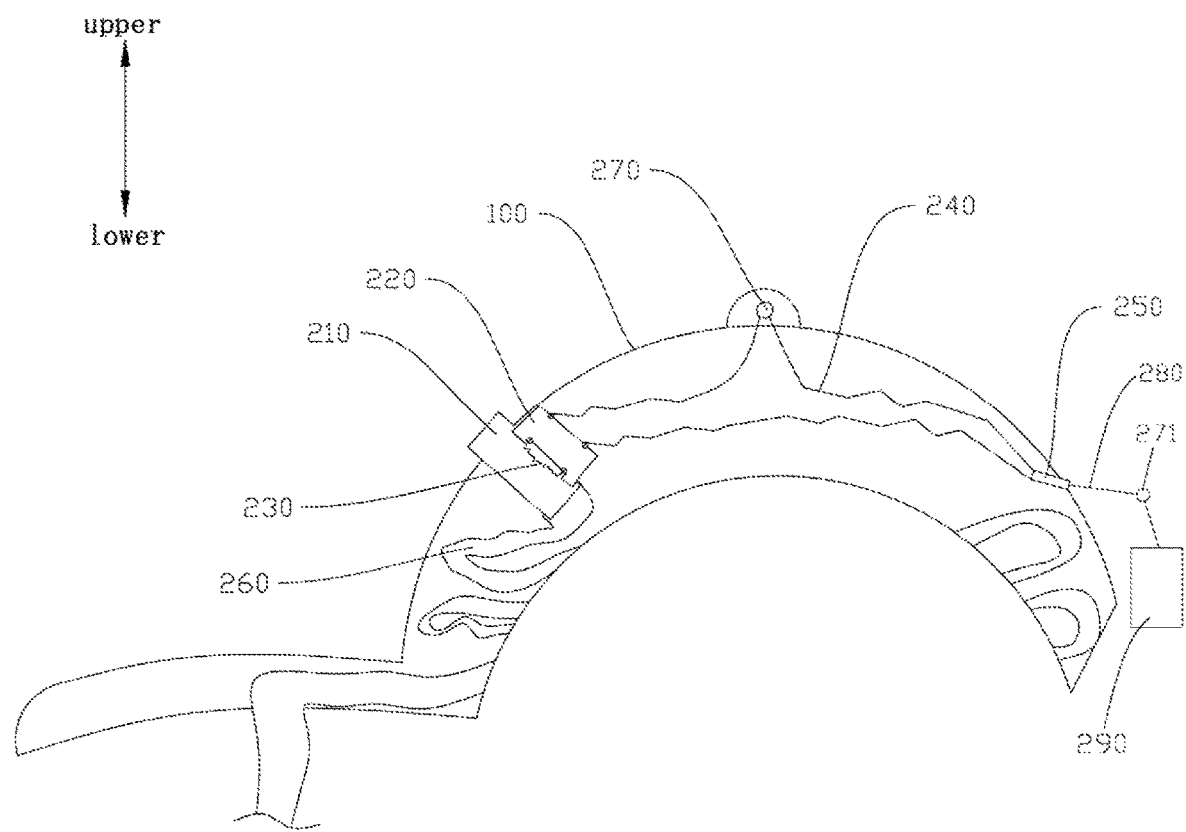
FIG. 3 is a schematic view of an assembly structure of a sunhat and a heating component according to an embodiment of the disclosure.
Figure 4:
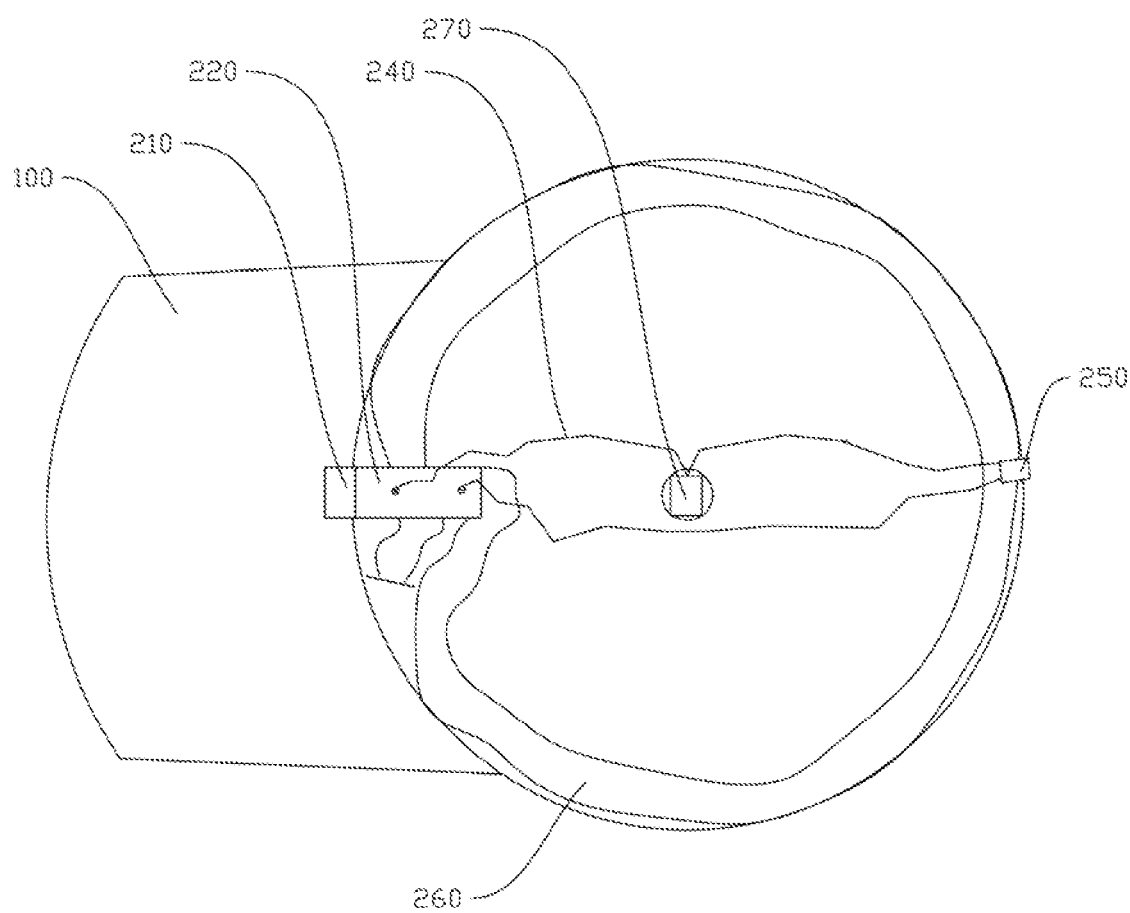
FIG. 4 is a top view of FIG. 3, wherein the USB data line, the second switch button, and the power source are not shown.

As shown in FIGS. 3 and 4, in some embodiments of the disclosure, a first switch button 270 for controlling the on/off of the circuit is connected in series on the electric wire 240, and the first switch button 270 is arranged on an outer surface of the sunhat 100. With such an arrangement, when in use, the wearer can control the circuit to turn on only by pressing the first switch button 270, so that the resistance wire 230 is energized to generate heat for disinfection. After use, the circuit can also be controlled to turn off by the first switch button 270, thereby stopping heating and saving energy consumption.

In some embodiments of the disclosure, the power source 290 is a power bank which may be electrically connected to the charge port 250 through a USB data line 280, and a second switch button 271 is arranged on the USB data line 280. Power is supplied by the power bank that is commonly used in the daily life, so it is convenient to improve a commercially-available mask with a breather valve 310 to obtain the mask provided in the embodiments of the disclosure. Thus, better protective effect can be achieved, the service life of the masks can be prolonged, the consumption of the existing commercially-available masks with a breather valve 310 can be reduced, and the current supply pressure of masks can be reduced. Moreover, by arranging the second switch button 271 on the USB data line 280, the safety performance of the embodiments of the disclosure is further improved. Accordingly, it is avoided that, when not in use, the first switch button 270 is pressed by mistake and the resistance wire 230 generates heat as usual, so that the waste of resources is reduced.

In some embodiments of the disclosure, the cooling tube 260 is an elbow tube which is wound around a body of the sunhat 100 for 2 to 4 times. With such an arrangement, the cooling tube 260 is wound around the body of the sunhat 100 in a coil manner. Thus, under the premise of ensuring the high-temperature disinfected air to be cooled to the normal temperature, the footprint is reduced.

In some embodiments of the disclosure, the sunhat 100 is a peaked cap, the cooling tube 260 is wound around a body of the peaked cap for 4 times, and an air outlet end of the cooling tube 260 extends out of a peaked portion of the peaked cap to be communicated with an air inlet port of the rubber hose 400. With such an arrangement, due to the guidance of the peaked portion of the peaked cap, it is convenient for the air outlet tube of the cooling tube 260 to extend out to be communicated with the rubber hose 400. Meanwhile, since the cooling tube 260 surrounds the body of the peaked cap by four circles, the flow path of the high-temperature disinfected air in the cooling tube 260 is extended, so that the temperature of the air flowing into the rubber hose 400 is reduced to 30° C. for normal inhalation by the wearer without causing any discomfort.

Figure 5:
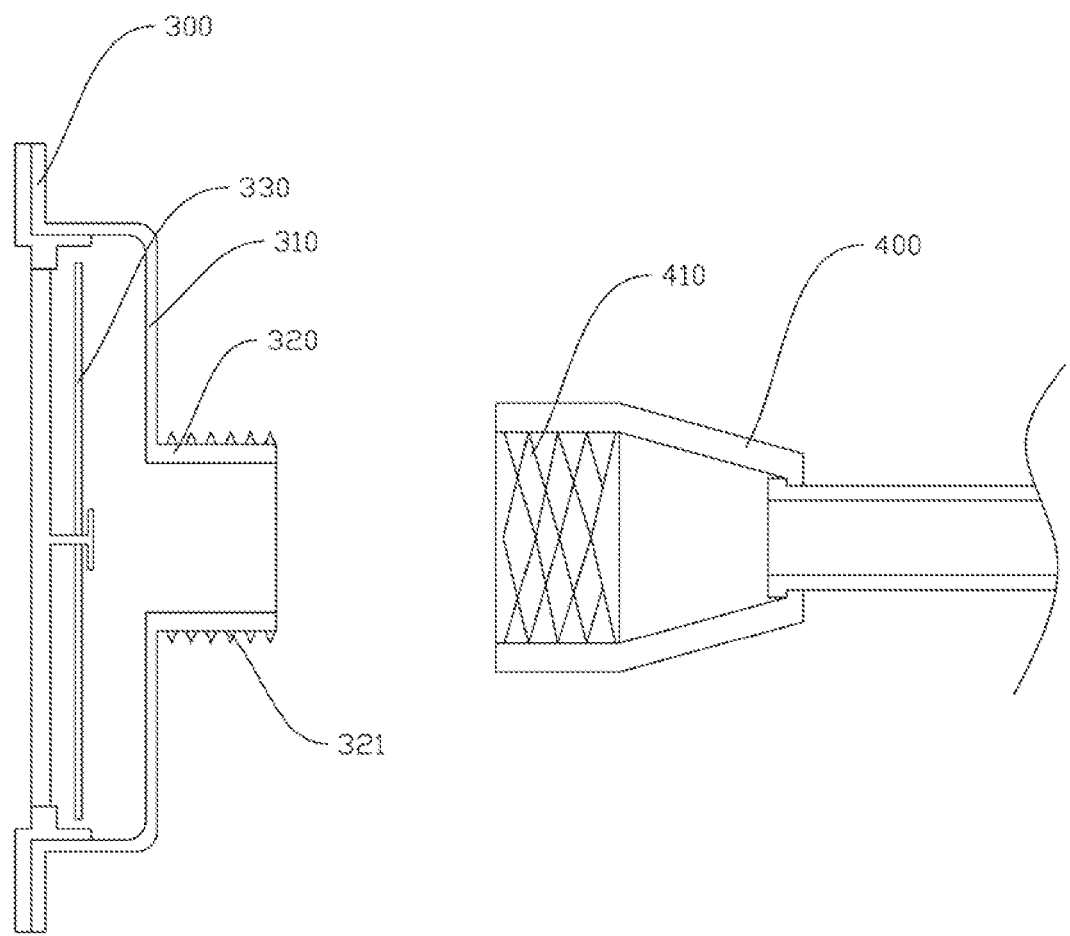
FIG. 5 is a schematic view of a disassembly structure of a mask body and a rubber hose according to an embodiment of the disclosure.
Figure 6:
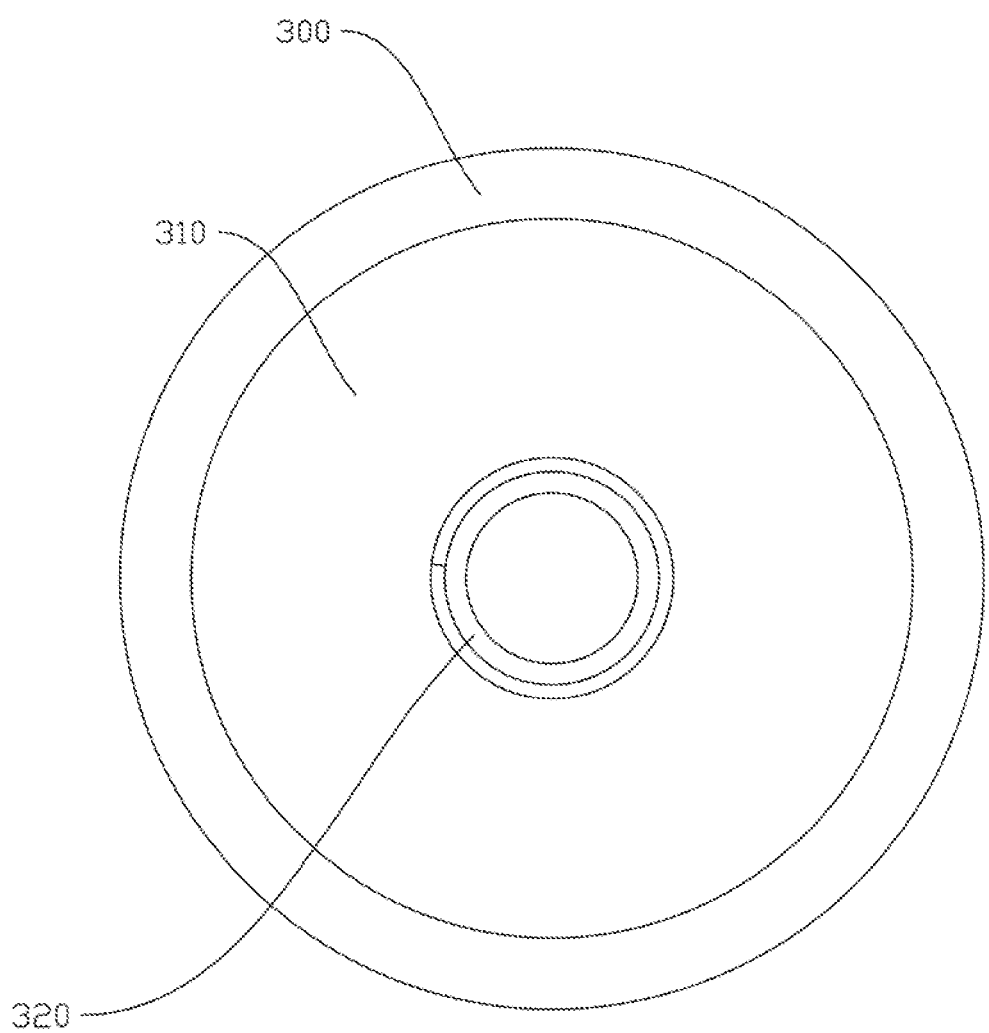
FIG. 6 is a schematic structural diagram of the mask body according to an embodiment of the disclosure.

As shown in FIG. 5, in some embodiments of the disclosure, an air inlet/outlet tube 320 is arranged in a middle portion of the breather valve 310, an outer thread 321 is arranged at an end of the air inlet/outlet tube 320 away from the breather valve 310, and an inner thread 410 matched with the outer thread 321 is arranged in an air outlet end of the rubber hose 400. Through a threaded connection of the outer thread 321 with the inner thread 410, a firm connection between the air inlet/outlet tube 320 and the rubber hose 400 is realized, and it is avoided that the protective effect cannot be achieved due to the separation from each other of the rubber hose 400 and the air inlet/outlet tube 321 at their connection when in use. Thus, disassembly or assembly can be easily performed for replacement and maintenance. In addition, when the wearer exhales, the exhaled air is transmitted to the rubber hose 400 and the cooling tube 260 through the breather valve 310, then sterilized at a high temperature in the high-temperature hose, and discharged to the outside. After a person carrying virus wears the mask provided by the embodiments of the disclosure, the possibility of infecting other persons can be reduced.

In some embodiments of the disclosure, the high-temperature microtube 210 is a ceramic tube, and a heat preservation layer is arranged on an outer surface of the ceramic tube. Since the ceramic tube has low heat conductivity, heat generated by the resistance wire 230 can be prevented from fast diffusion, and it is ensured that the temperature in the high-temperature microtube 210 can be always maintained at about 200° C., so as to completely kill the NCP in the air in the high-temperature microtube 210. In addition, by arranging the heat preservation layer on the outer surface of the ceramic tube, the heat loss can be reduced, and a thermal insulation effect can be achieved, thus avoiding high temperature scalding.

In some embodiments of the disclosure, the cooling tube 260 is a copper tube, and a thermal insulating layer is arranged on an outer surface of the copper tube. Since the copper tube has good heat conductivity, it is convenient for the high-temperature disinfected air to be cooled to the normal temperature rapidly. Moreover, by arranging a thick rubber thermal insulating layer on the outer surface of the copper tube, high-temperature scalding can be prevented. Of course, the specific material of the cooling tube 260 is not limited herein. According to actual needs, the cooling tube 260 may be a copper tube.

In some embodiments of the disclosure, the mask body 300 is a KN95 protective mask with a breather valve 310. The KN95 protective mask with the breather valve 310 itself has a good filtering effect. In combination with the high-temperature disinfection effect of the high-temperature microtube 210, a better protective effect is achieved in the embodiments of the disclosure, and the duration of the protective effect is prolonged. Accordingly, the consumption of the existing commercially-available masks with a breather valve 310 is reduced, and the current supply pressure of masks can be reduced.

In some embodiments of the disclosure, the high-temperature microtube 210 has a length of 20 mm, an outer diameter of 4 mm and a wall thickness of 0.5 mm. With such a dimensional arrangement, it is ensured that the resistance wire 230 can be rapidly heated after being energized, so that the temperature in the high-temperature microtube 210 reaches about 200° C., and the disinfection effect is improved.

The foregoing description merely shows the preferred embodiments of the disclosure and is not intended to limit the disclosure. Various alterations and changes can be made to the disclosure by those skilled in the art. Any modifications, equivalent replacements and improvements made without departing from the concept and principle of the disclosure shall fall into the protection scope of the disclosure.

We claim:

1. A high-temperature virus-killing mask, comprising:
   a sunhat;
   a heating component, comprising:
      a high-temperature microtube arranged in the sunhat and provided with:
         a positive electrode at an upper end of the high-temperature microtube and close to a middle portion of the high-temperature microtube,
         a negative electrode at a lower end of the high-temperature microtube and close to the middle portion of the high-temperature microtube,
         a resistance wire in the high-temperature microtube, with two ends electrically connected to the positive electrode and the negative electrode, respectively, and
      a base arranged in the sunhat and provided with:
         a positive terminal in which the positive electrode is clamped, and
         a negative terminal in which the negative electrode is clamped;
      wherein the base is electrically connected, by an electric wire, to a charge port which, when in use, is electrically connected to a power source; and
      wherein the high-temperature microtube includes an upper end portion extending outside the sunhat to facilitate air inhalation and a lower end portion communicated with a cooling tube; and
   a mask body with a breather valve arranged on an outer surface of the mask body, the breather valve being communicated with a rubber hose, and an air inlet end of the rubber hose being connected to an air outlet end of the cooling tube.

2. The high-temperature virus-killing mask of claim 1, wherein a first switch button for controlling on/off of the circuit is connected in series on the electric wire, and the first switch button is arranged on an outer surface of the sunhat.

3. The high-temperature virus-killing mask of claim 1, wherein the power source is a power bank which is electrically connected to the charge port through a USB data line, and a second switch button is arranged on the USB data line.

4. The high-temperature virus-killing mask of claim 1, wherein the cooling tube is an elbow tube which is wound around a body of the sunhat for 2 to 4 times.

5. The high-temperature virus-killing mask of claim 4, wherein the sunhat is a peaked cap, the cooling tube is wound around a body of the peaked cap for 4 times, and the air outlet end of the cooling tube extends out from a peaked portion of the peaked cap to be communicated with an air inlet port of the rubber hose.

6. The high-temperature virus-killing mask of claim 1, wherein an air inlet/outlet tube is arranged in a middle portion of the breather valve, an outer thread is arranged at an end of the air inlet/outlet tube away from the breather valve, and an inner thread matched with the outer thread is arranged in an air outlet end of the rubber hose.

7. The high-temperature virus-killing mask of claim 1, wherein the high-temperature microtube is a ceramic tube with a heat preservation layer arranged on an outer surface of the ceramic tube.

8. The high-temperature virus-killing mask of claim 1, wherein the cooling tube is a copper tube with a thermal insulating layer arranged on an outer surface of the copper tube.

9. The high-temperature virus-killing mask of claim 1, wherein the mask body is a KN95 protective mask with a breather valve.

10. The high-temperature virus-killing mask of claim 1, wherein the high-temperature microtube has a length of 20 mm, an outer diameter of 4 mm and a wall thickness of 0.5 mm.

* * * * *